(12) United States Patent
Barker

(10) Patent No.: US 9,415,212 B2
(45) Date of Patent: Aug. 16, 2016

(54) SIDE LOADING LEAD ANCHOR AND METHODS OF MAKING AND USING THEREOF

(71) Applicant: BOSTON SCIENTIFIC NEUROMODULATION CORPORATION, Valencia, CA (US)

(72) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/630,124

(22) Filed: Feb. 24, 2015

(65) Prior Publication Data

US 2015/0246216 A1  Sep. 3, 2015

Related U.S. Application Data

(60) Provisional application No. 61/946,162, filed on Feb. 28, 2014.

(51) Int. Cl.
*A61N 1/00* (2006.01)
*A61N 1/05* (2006.01)

(52) U.S. Cl.
CPC ....... *A61N 1/0558* (2013.01); *A61N 2001/0582* (2013.01)

(58) Field of Classification Search
USPC .......................................................... 607/116
See application file for complete search history.

(56) References Cited

U.S. PATENT DOCUMENTS

| | | |
|---|---|---|
| 3,866,615 A | 2/1975 | Hewson |
| 4,141,752 A | 2/1979 | Shipko |
| 4,276,882 A | 7/1981 | Dickhudt et al. |
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,158,097 A | 10/1992 | Christlieb |
| 5,228,248 A | 7/1993 | Haddock |
| 5,376,108 A | 12/1994 | Collins et al. |

(Continued)

FOREIGN PATENT DOCUMENTS

| | | |
|---|---|---|
| EP | 85417 A1 | 8/1983 |
| EP | 0597213 A1 | 5/1994 |

(Continued)

*Primary Examiner* — Nicole F Johnson
(74) *Attorney, Agent, or Firm* — Lowe Graham Jones PLLC; Bruce E. Black

(57) ABSTRACT

An implantable lead anchor includes a first anchor housing, a second anchor housing, an armature, a spindle, and a locking arrangement. The first and second anchor housing each includes at least one channel to hold a portion of a lead. The armature is coupled to the first and the second anchor housings and holds the first and second anchor housings in a spaced-apart arrangement. A spindle is rotatably disposed on the armature and between the first and second anchor housing. In addition, the spindle includes a third channel to receive and hold a portion of a lead. The locking arrangement is formed on the spindle and at least one of the first or second anchor housing. The locking arrangement maintains the spindle in a rotated position relative to the first and second anchor housing when the locking arrangement is activated.

20 Claims, 7 Drawing Sheets

(56) References Cited

U.S. PATENT DOCUMENTS

| | | | |
|---|---|---|---|
| 5,484,445 | A | 1/1996 | Knuth |
| 5,865,843 | A | 2/1999 | Baudino |
| 5,957,968 | A | 9/1999 | Belden et al. |
| 6,181,969 | B1 | 1/2001 | Gord |
| 6,192,279 | B1 | 2/2001 | Barreras, Sr. et al. |
| 6,360,750 | B1 | 3/2002 | Gerber et al. |
| 6,473,654 | B1 | 10/2002 | Chinn |
| 6,516,227 | B1 | 2/2003 | Meadows et al. |
| 6,606,523 | B1 | 8/2003 | Jenkins |
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,792,314 | B2 | 9/2004 | Byers et al. |
| 6,847,849 | B2 | 1/2005 | Mamo et al. |
| 6,901,287 | B2 | 5/2005 | Davis et al. |
| 6,978,180 | B2 | 12/2005 | Tadlock |
| 6,984,145 | B1 | 1/2006 | Lim |
| 7,069,083 | B2 | 6/2006 | Finch et al. |
| 7,072,719 | B2 | 7/2006 | Vinup et al. |
| 7,161,461 | B1 | 1/2007 | Nelson |
| 7,244,150 | B1 | 7/2007 | Brase et al. |
| 7,343,202 | B2 | 3/2008 | Mrva et al. |
| 7,402,076 | B1 * | 7/2008 | Lim ................ A61N 1/3752 439/462 |
| 7,437,193 | B2 | 10/2008 | Parramon et al. |
| 7,447,546 | B2 | 11/2008 | Kim et al. |
| 7,610,102 | B2 | 10/2009 | Kowalczyk |
| 7,672,734 | B2 | 3/2010 | Anderson et al. |
| 7,761,165 | B1 | 7/2010 | He et al. |
| 7,787,960 | B2 | 8/2010 | Lubenow |
| 7,848,803 | B1 | 12/2010 | Jaax et al. |
| 7,853,321 | B2 | 12/2010 | Jaax et al. |
| 7,860,568 | B2 * | 12/2010 | Deininger ............ A61N 1/3752 607/37 |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |
| 8,224,451 | B2 | 7/2012 | Jaax et al. |
| 8,229,573 | B2 | 7/2012 | Chen et al. |
| 8,315,704 | B2 | 11/2012 | Jaax et al. |
| 8,364,278 | B2 | 1/2013 | Pianca et al. |
| 2001/0000187 | A1 | 4/2001 | Peckham et al. |
| 2002/0107554 | A1 | 8/2002 | Biggs et al. |
| 2003/0078623 | A1 | 4/2003 | Weinberg et al. |
| 2003/0208247 | A1 | 11/2003 | Spinelli et al. |
| 2004/0059392 | A1 | 3/2004 | Parramon et al. |
| 2005/0165465 | A1 | 7/2005 | Pianca et al. |
| 2005/0283202 | A1 | 12/2005 | Gellman |
| 2005/0288760 | A1 | 12/2005 | Machado et al. |
| 2006/0127158 | A1 | 6/2006 | Olson et al. |
| 2006/0161235 | A1 | 7/2006 | King |
| 2006/0173520 | A1 | 8/2006 | Olson |
| 2006/0206162 | A1 | 9/2006 | Wahlstrand et al. |
| 2007/0050005 | A1 | 3/2007 | Lauro |
| 2007/0078399 | A1 | 4/2007 | Olson |
| 2007/0150036 | A1 | 6/2007 | Anderson |
| 2007/0219595 | A1 | 9/2007 | He |
| 2007/0255369 | A1 | 11/2007 | Bonde et al. |
| 2008/0071320 | A1 | 3/2008 | Brase |
| 2008/0091255 | A1 | 4/2008 | Caparso et al. |
| 2008/0140169 | A1 | 6/2008 | Imran |
| 2008/0172116 | A1 | 7/2008 | Mrva et al. |
| 2008/0183241 | A1 | 7/2008 | Bedenbaugh |
| 2008/0183253 | A1 | 7/2008 | Bly |
| 2008/0228251 | A1 | 9/2008 | Hill |
| 2008/0243220 | A1 | 10/2008 | Barker |
| 2008/0312712 | A1 | 12/2008 | Penner |
| 2009/0018601 | A1 | 1/2009 | Deininger et al. |
| 2009/0112272 | A1 | 4/2009 | Schleicher et al. |
| 2009/0198312 | A1 | 8/2009 | Barker |
| 2009/0254151 | A1 | 10/2009 | Anderson et al. |
| 2009/0270940 | A1 | 10/2009 | Deininger |
| 2010/0174240 | A1 | 7/2010 | Wells et al. |
| 2010/0274336 | A1 | 10/2010 | Nguyen-Stella et al. |
| 2010/0312319 | A1 | 12/2010 | Barker |
| 2011/0022142 | A1 | 1/2011 | Barker et al. |
| 2011/0060395 | A1 | 3/2011 | Cantlon |
| 2011/0178573 | A1 | 7/2011 | Nguyen-Stella et al. |
| 2012/0150202 | A1 | 6/2012 | Chen et al. |
| 2012/0185027 | A1 | 7/2012 | Pianca et al. |
| 2012/0232626 | A1 | 9/2012 | Daglow |
| 2012/0277670 | A1 | 11/2012 | Goetz |
| 2012/0330355 | A1 | 12/2012 | Finley et al. |
| 2013/0149031 | A1 * | 6/2013 | Changsrivong ......... F16B 17/00 403/376 |
| 2013/0204336 | A1 | 8/2013 | Sharma |
| 2015/0005856 | A1 | 1/2015 | Pianca et al. |
| 2015/0045865 | A1 | 2/2015 | Nageri et al. |
| 2015/0051674 | A1 | 2/2015 | Barner et al. |
| 2015/0051675 | A1 | 2/2015 | Barner |

FOREIGN PATENT DOCUMENTS

| | | |
|---|---|---|
| WO | 9833551 A1 | 8/1998 |
| WO | 99/53994 | 10/1999 |
| WO | 00/13743 A2 | 3/2000 |
| WO | 00/64535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2013112920 A1 | 8/2013 |

* cited by examiner

SIDE LOADING LEAD ANCHOR AND METHODS OF MAKING AND USING THEREOF

CROSS-REFERENCE TO RELATED APPLICATIONS

This application claims the benefit under 35 U.S.C. §119 (e) of U.S. Provisional Patent Application Ser. No. 61/946,162, filed Feb. 28, 2014, which is incorporated herein by reference.

FIELD

The present invention is directed to the area of implantable electrical stimulation systems and methods of making and using the systems. The present invention is also directed to a side loading anchor for receiving one or more leads, as well as methods of making and using the anchor with leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Often leads are anchored at one or more places within the body to prevent or reduce the movement of the lead or stimulator electrodes after implantation. Such undesired movement of the leads may lead to: (1) damage to surrounding tissue; (2) movement of the stimulator electrodes out of their desired positions in such a way as to reduce effectiveness of treatment; or (3) interference or interruption in the connections between the stimulator electrodes and the control module.

BRIEF SUMMARY

In one embodiment, an implantable lead anchor includes a first anchor housing including at least one first lead receiving channel and a second anchor housing including at least one second lead receiving channel. Additionally, the lead anchor includes an armature coupled to the first anchor housing and the second anchor housing and holding the first and second anchor housings in a spaced-apart arrangement. Moreover, the lead anchor includes a spindle configured and arranged to be rotatably disposed on the armature and between the first and second anchor housings. The spindle further includes at least one third lead receiving channel configured and arranged to receive and hold a portion of a lead within the at least one third lead receiving channel. In addition, a locking arrangement is formed on the spindle and at least one of the first anchor housing or second anchor housing. The locking arrangement is configured and arranged to maintain the spindle in a rotated position relative to the first and second anchor housing when the locking arrangement is activated.

In another embodiment, a kit includes the implantable lead anchor described above and at least one electrical stimulation lead. The implantable lead anchor is configured and arranged to receive a portion of one of the at least one electrical stimulation lead in the lead channel.

In yet another embodiment, a method of implanting an electrical stimulation lead includes side loading a portion of a first electrical stimulation lead into a one of the at least one third lead receiving channel of the implantable lead anchor described above. Additionally, the method includes rotating the spindle to lock the first electrical stimulation lead in the implantable lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed a side loading anchor for receiving one or more leads, as well as methods of making and using the anchor with leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
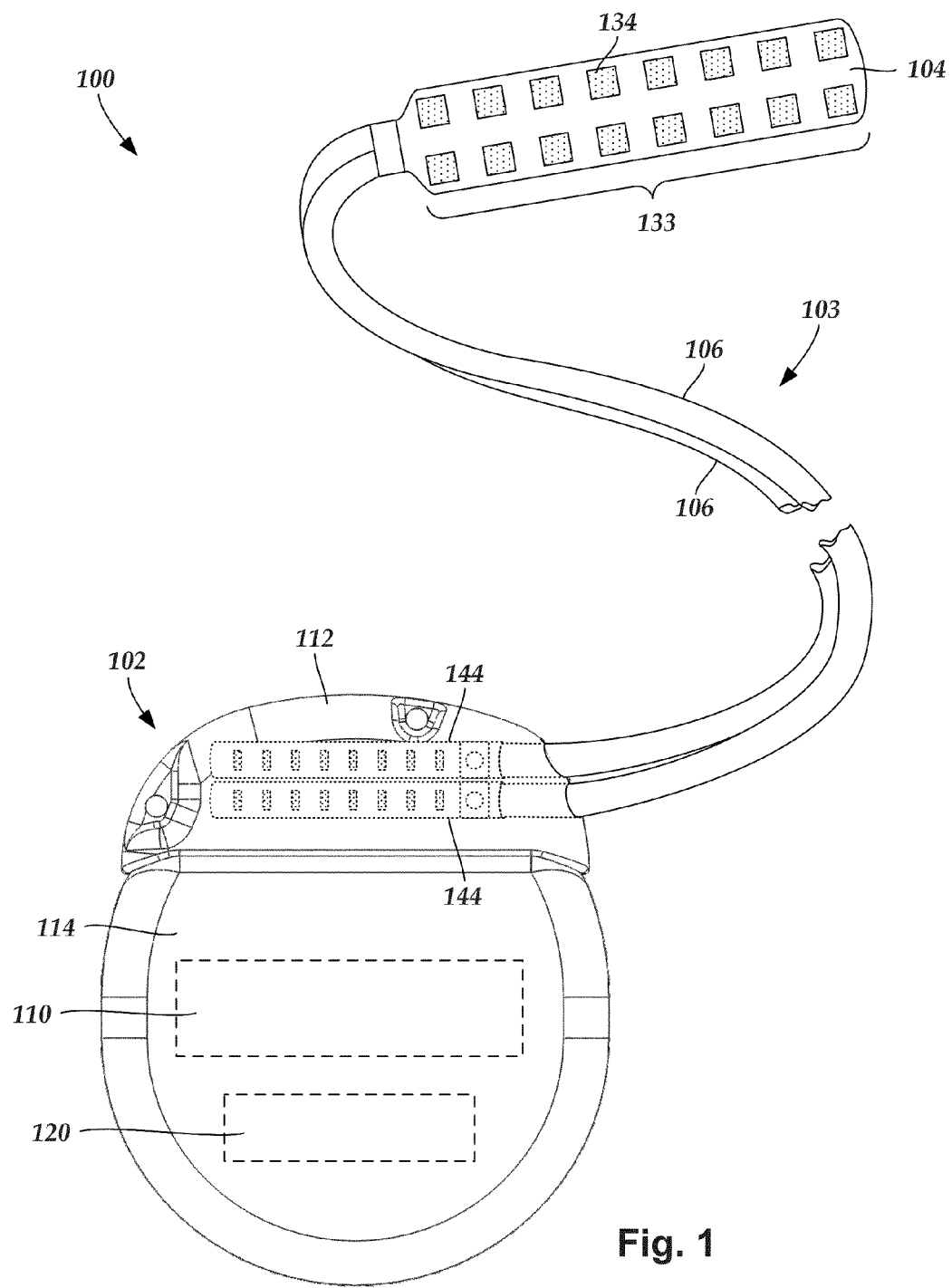
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight, or more lead bodies 106. An array 133 of electrodes, such as electrode 134, is disposed on the paddle body 104, and an array of terminals (e.g., 310 in FIGS. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
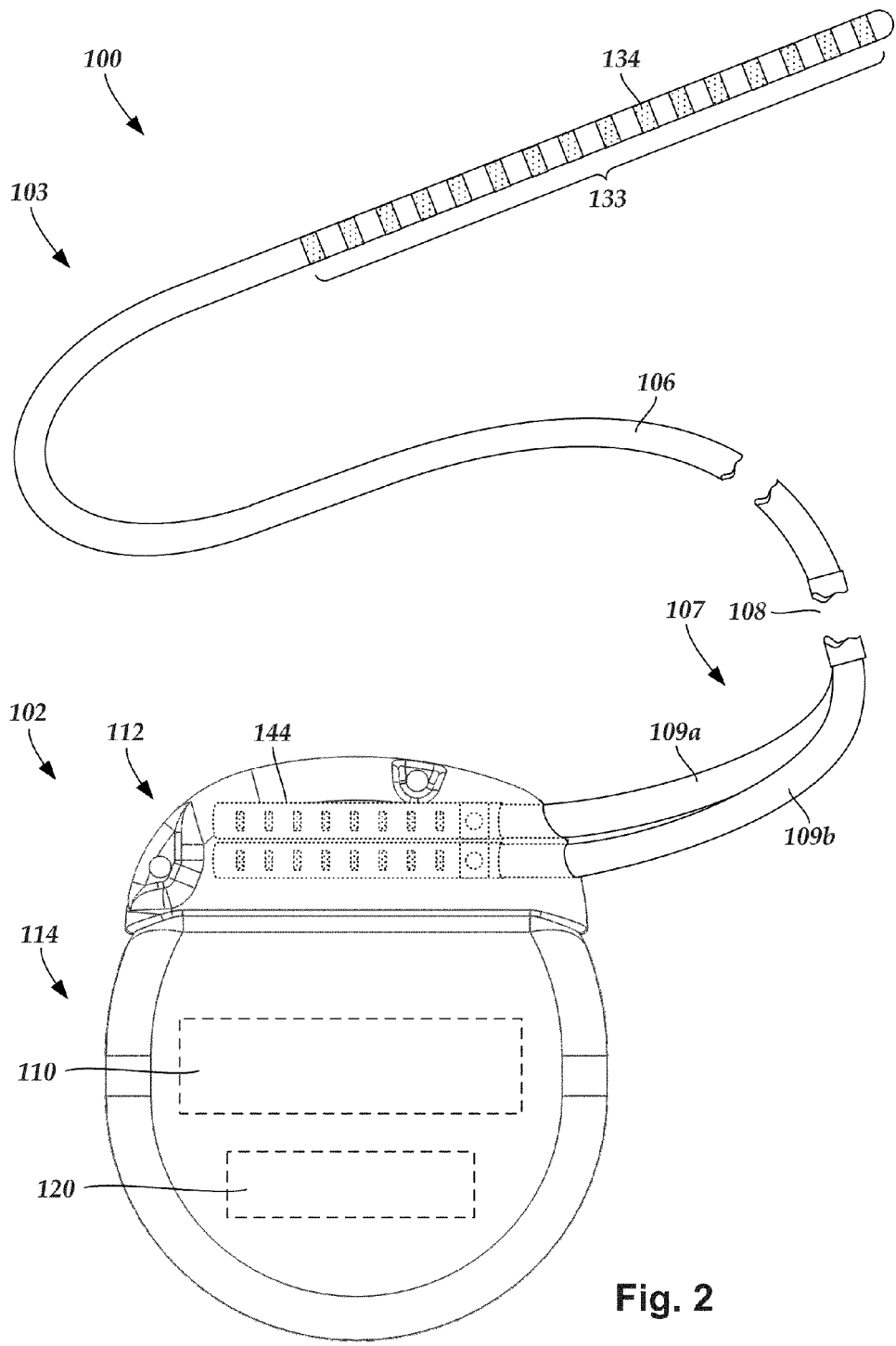
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled.

Figure 3A:
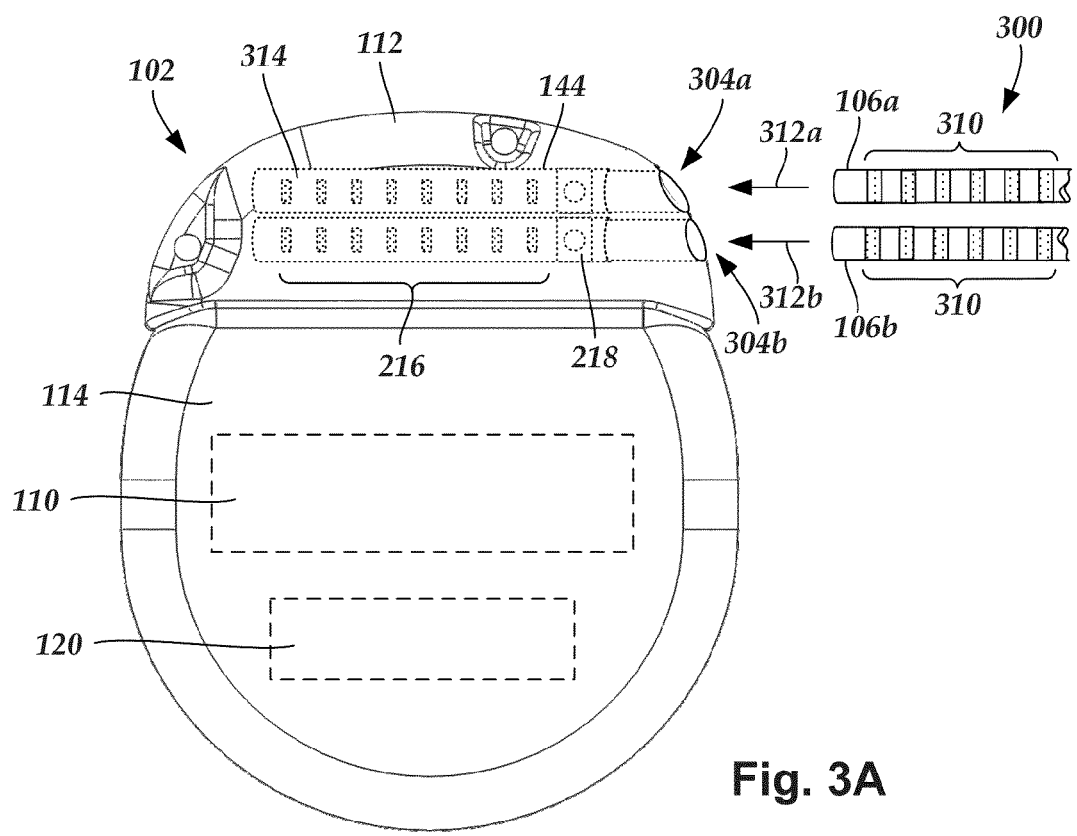
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
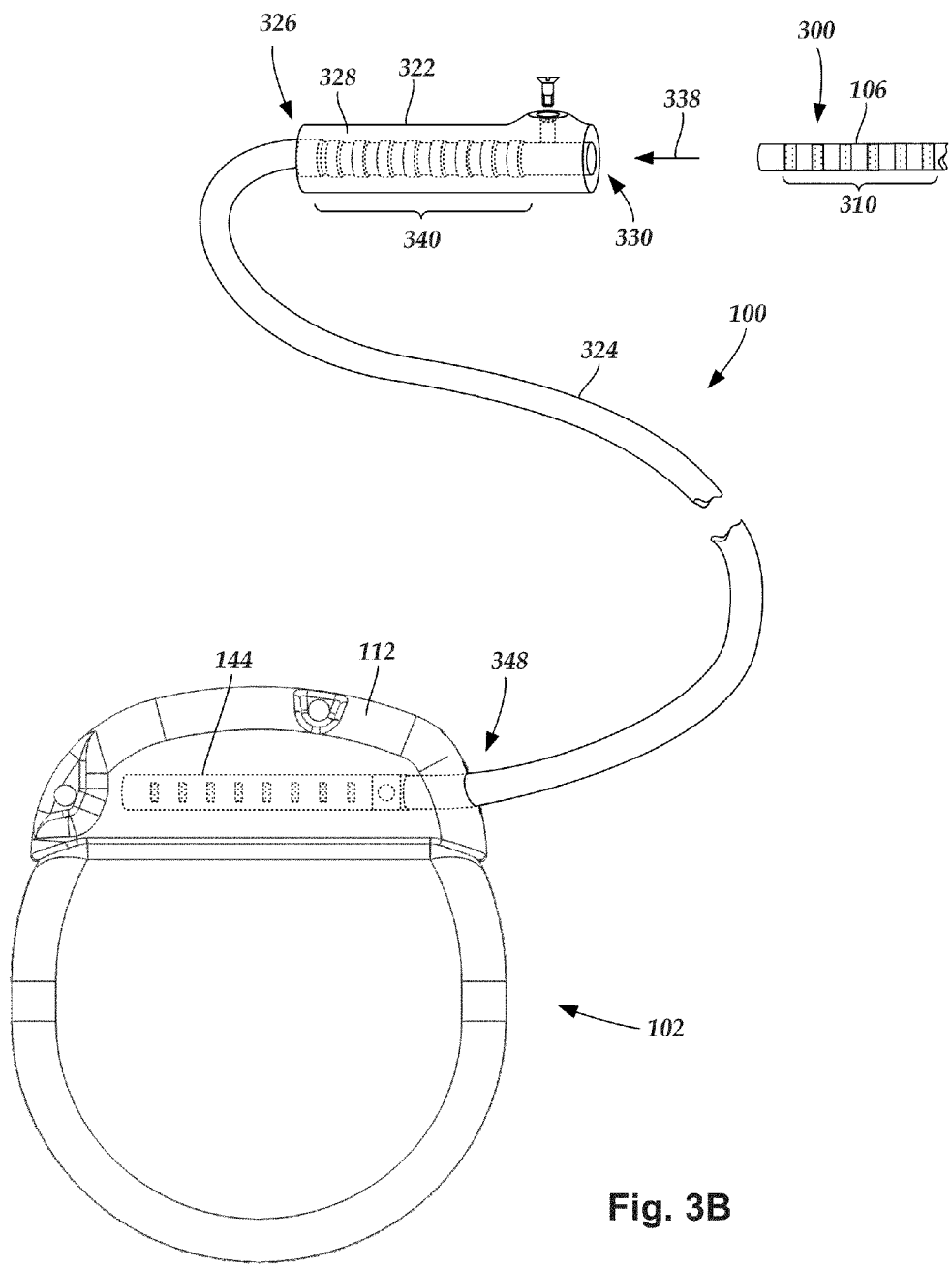
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4A:
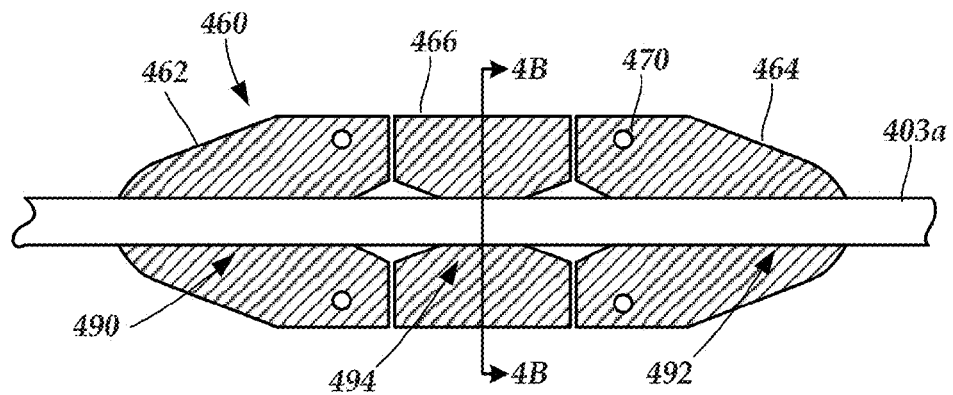
FIG. 4A is a schematic side view of a side loading lead anchor in a loading position, according to the invention.
Figure 4B:
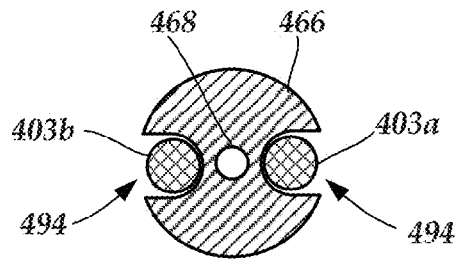
FIG. 4B is a schematic cross-sectional view of the side loading lead anchor of FIG. 4A taken along line 4B-4B, according to the invention.

After implantation, there is a risk that the body of the lead (e.g., 103 in FIG. 1) or the lead extension (e.g., 324 in FIG. 3B) may move inadvertently from a desired location within a patient's body. To prevent or reduce the inadvertent movement of the lead 103 or the lead extension 324 (also referred to as "lead migration"), one or more lead anchors may hold the lead 103 or the lead extension 324 in place within the patient tissue. FIGS. 4A and 4B illustrate a side loading lead anchor 460 to hold at least one lead within a patient's body.

FIG. 4A is a schematic side view of the side loading lead anchor 460 in a loading position. FIG. 4B is a schematic cross-sectional view of the side loading lead anchor 460 of FIG. 4A taken along line 4B-4B. In some embodiments, as shown, the lead anchor 460 has a substantially cylindrical shape. Other suitable shapes of the lead anchor 460 include spheroidal, polygonal, or any other shape, preferably with rounded edges or vertices. The lead anchor 460 has suitable dimensions to be implanted within a patient's body. In some embodiments, the length of the lead anchor 460 ranges from 1 cm to 5 cm. In other embodiments, the length of the lead anchor 460 ranges from 2 cm to 3 cm. In addition, in some embodiments, the largest radial diameter of the lead anchor 460 ranges from 4 mm to 30 mm. In other embodiments, the largest radial diameter of the lead anchor 460 ranges from 5 mm to 15 mm.

The lead anchor 460 includes a first anchor housing 462, a second anchor housing 464, a spindle 466, and an armature 468 (shown in FIG. 4B). In some embodiments, the first and the second anchor housings 462 and 464 have a substantially cylindrical shape. Other suitable shapes for the first and the second anchor housings 462 and 464 includes conical, frustum, hemispheroidal, polygonal, and any other shape, preferably with rounded or smooth atraumatic edges and vertices.

In at least some embodiments, the armature 468 is coupled to the first anchor housing 462 and the second anchor housing 464. The armature 468 can be a cylindrical shaft or tube. The armature 468 maintains the first and second anchor housings 462 and 464 in a spaced-apart arrangement. For example, in some embodiments, the armature 468 is fixedly disposed in a central lumen (not shown) that extends through a central axis of the first and second housing 462 and 464. In other embodiments, the armature 468 is attached to the laterally opposing surfaces of the first and second housings 462 and 464 by any suitable biocompatible attachment means such as adhesives, screws, rivets, or the like. In other embodiments, the armature 468 is molded as a part of one or both of the first and second housings 462 and 464.

As shown in FIG. 4A, there is a gap between the first and second anchor housings 462 and 464, where the spindle 466 is located. The spindle 466 is rotatably disposed on the armature 468 between the first anchor housing 462 and the second anchor housing 464.

In at least some embodiments, as shown, the spindle 466 has a substantially cylindrical shape. Any other suitable shape, preferably having rounded or smooth atraumatic edges and vertices, can be used to make the spindle 466. For example, in some embodiments, the spindle 466 has a hexagonal shape with smooth edges and vertices.

In some embodiments, a method of making the lead anchor 460 includes fixedly attaching the first anchor housing 462 or the second anchor housing 464 to the armature 468. Then, the spindle 466 is disposed on the armature 468 followed by fixed attachment of the other anchor housing to the armature 468.

In some embodiments, to prevent or reduce any impediment in rotation of the spindle 466, the first and the second anchor housings 462 and 464 has a generally flat surface facing the spindle 466. Similarly, the spindle 466 has a generally flat surface facing each of the first and the second anchor housings 462 and 464.

The lead anchor 460 is typically sutured to the patient's tissue. To facilitate suturing of the lead anchor 460, one or both of the first and second anchor housing 462 and 464 has at least one suture hole 470. In some embodiments, the first and the second anchor housings 462 and 464 have two or more suture holes 470 to facilitate suturing of the lead anchor 460.

In at least some embodiments, the lead anchor (such as lead anchor 460 in FIG. 4A) is made of a MRI-compatible material. For examples, the first anchor housing 462, second anchor housing 464, the spindle 466 and armature 468 can be made of a rigid biocompatible polymeric material, such as, polytetrafluoroethylene (PTFE or TEFLON™), polyethylene terephthalate (PET or DACRON™), polyvinyl chloride (PVC), polycarbonate, polyether ether ketone (PEEK), or the like or combinations thereof.

In some embodiments, the central lumen (not shown) of the spindle 466 and the surface of the armature 468 in contact with the central lumen of the spindle 466 are coated with a biocompatible material that reduces friction. Some examples of such friction-reducing materials include, but are not limited to, polytetrafluoroethylene (PTFE), tetrafluoroethylene (TFE), polyethylene terephthalate (PET or DACRON™) or the like or combinations thereof.

The lead anchor 460 secures leads or lead extensions by engaging them in one or more side loading channels. As shown in FIGS. 4A and 4B, in at least some embodiments, the first anchor housing 462 includes a first pair of lead receiving channels 490 for securing two leads on two laterally opposing sides along the circumference of the lead anchor 460. Similarly, the second anchor housing 464 includes a second pair of lead receiving channels 492, and the spindle 466 has a third pair of lead receiving channels 494. In a loading position, the channels 490, 492, and 494 are coaxially arranged to form two substantially straight channels in which the two leads 403a and 403b can be loaded and secured to the lead anchor 460.

In some embodiments, the channels 490, 492, and 494 have constricted openings (not shown) at the laterally opposing sides of the lead anchor 460, such that an operator needs to apply a threshold force to push or pull leads 403a and 403b in and out of the channels 490, 492, and 494 through the constricted openings. The threshold force prevents or reduces the probability of the leads 403a and 403b inadvertently disengaging from the channels 490, 492, and 494.

In at least some embodiments, after loading the leads 403a and 403b in the channels 490, 492, and 494, the spindle 466 is rotated clockwise or counter-clockwise, to misalign the channels 494 from the channels 490 and 492 and introduce a kink or tortuous path to the leads 403a and 403b. In addition, the lead anchor 460 includes a locking arrangement (shown in FIGS. 6A-6B, and FIG. 7), which is configured and arranged to lock the spindle 466 in a rotated position and maintain the kink introduced in the leads 403a and 403b (shown in FIGS. 5A and 5B). Moreover, in some embodiments, the spindle 466 includes markings to indicate the extent of rotation and the locking position.

Figure 5A:
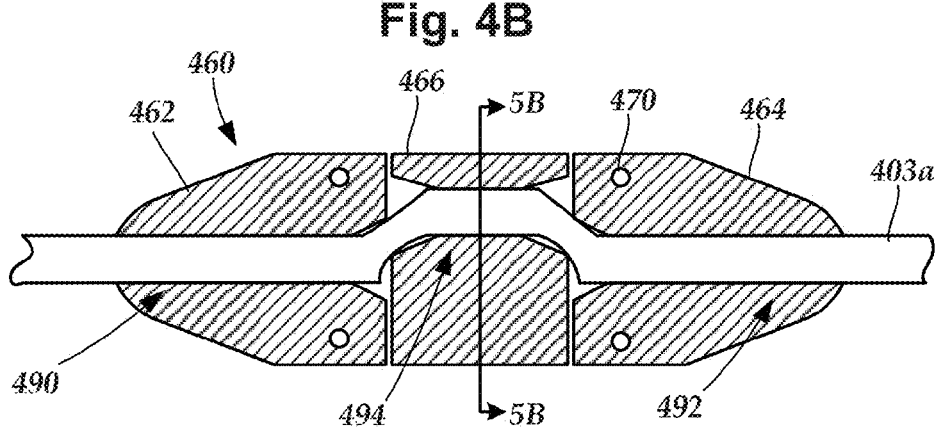
FIG. 5A is a schematic side view of a side loading lead anchor in a locked position, according to the invention.
Figure 5B:
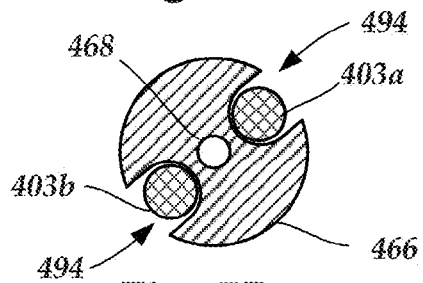
FIG. 5B is a schematic cross-sectional view of the side loading lead anchor of FIG. 5A taken along line 5B-5B, according to the invention.

FIGS. 5A and 5B illustrate the spindle 466 in the rotated and locked position. FIG. 5A is a schematic side view of the side loading lead anchor 460 in the locked position, and FIG. 5B is a schematic cross-sectional view of the side loading lead anchor 460 of FIG. 5A taken along line 5B-5B. As shown, the spindle 466 is maintained in the rotated position relative to the first and second anchor housing 462 and 464. In at least some embodiments, rotation of the spindle 466 creates a tortuous path for the leads 403a, 403b through the lead anchor 460. The rotation of the spindle 466 can introduce a kink in the leads 403a and 403b which increases friction between the leads 403a and 403b and the lead receiving channels 490, 492, and 494. The increased friction prevents or reduces disengagement or sliding of the leads 403a and 403b within the channels 490, 492, and 494.

In some instances, rotation of the spindle 466 might cause longitudinal displacement of the distal or proximal portion of the leads 403a and 403b. Longitudinal displacement of the distal portion of the leads 403a and 403b could result in inadvertent displacement or dislodgement of the electrodes 134 from the patient's tissue. To prevent or reduce longitudinal displacement of the leads 403a and 403b in the distal direction, in some embodiments, the first anchor housing 462 or the second anchor housing 464 is positioned distally, facing towards the distal end of the leads 403a and 403b, with the channel of that particular anchor housing having an internal diameter selected to grip the portions of the leads 403a and 403b disposed in the channel. The smaller diameter of the channel allows the channel to hold the leads 403a and 403b more firmly. The firmly gripped distal end of the leads 403a and 403b in channels 490 restricts the longitudinal displacement of the leads 403a and 403b arising from rotation of the spindle 466.

Figure 6A:
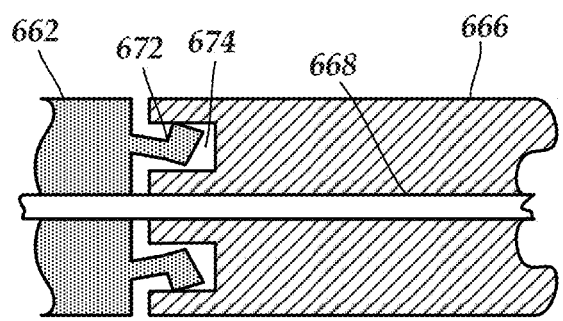
FIG. 6A is a schematic cross-sectional view of a locking arrangement with an annular recess and locking arms in an unlocked position, according to the invention.
Figure 6B:
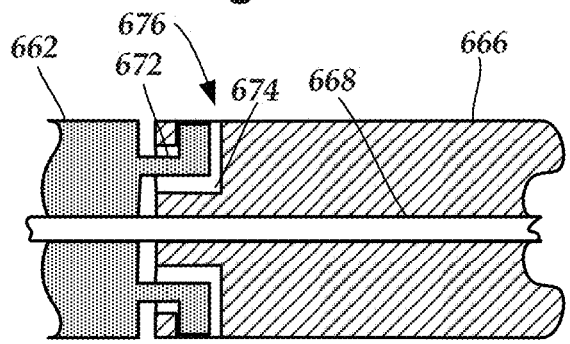
FIG. 6B is a schematic cross-sectional view of the locking arrangement of FIG. 6A with the locking arms in the locked position, according to the invention.

Any suitable locking arrangement can be used in the lead anchor 460. FIGS. 6A and 6B depict a locking arrangement that maintains the spindle 466 in a rotated position relative to the first and second anchor housings 462 and 464. FIG. 6A is a schematic cross-sectional view of a locking arrangement with an annular recess 674 and locking arm 672 in an unlocked position. As shown, in some embodiments, a first anchor housing 662 has one or more locking arms 672 extending or protruding out of a surface abutting a spindle 666. The locking arm(s) 672 extend into an annular recess 674 on the corresponding surface of the spindle 666. In other embodiments, the second anchor housing 664 or both first and second anchor housings 662 and 664 can have one or more locking arms 672. In yet other embodiments, the spindle 666 can have one or more locking arms 672 and the annular recess 674 can be disposed on the first or second anchor housings 662 or 664 (or both the first and second anchor housings).

In some embodiments, the locking arms 672 have a slightly longer length than the depth of the groove of the annular recess 674, thereby the locking arms 672 are slightly tensed in the annular recess 674. The locking arms 672 travel into the annular recess 674 upon rotation of the spindle 666 over the armature 668. FIG. 6B is a schematic cross-sectional view of the locking arrangement of FIG. 6A with the locking arms 672 in the locked position. The annular recess 674 includes at least one radial opening 676 at an angular displacement from the position of the lead receiving channels 494 (FIG. 4B). Radial opening 676 engages the locking arm 672 as the locking arm 672 travels in the annular recess 674 so that a portion of the locking arm extends into the radial opening. Upon engaging with the radial opening 676, the locking arm 672 restricts the rotational movement of the spindle 666, thereby, locking the spindle 666 in a rotated position. In some embodiments, the above discussed locking arrangement can be unlocked by pushing the locking arm 672 out of the radial opening 676 and into the annular recess 674 and then rotating the spindle 666.

Figure 7:
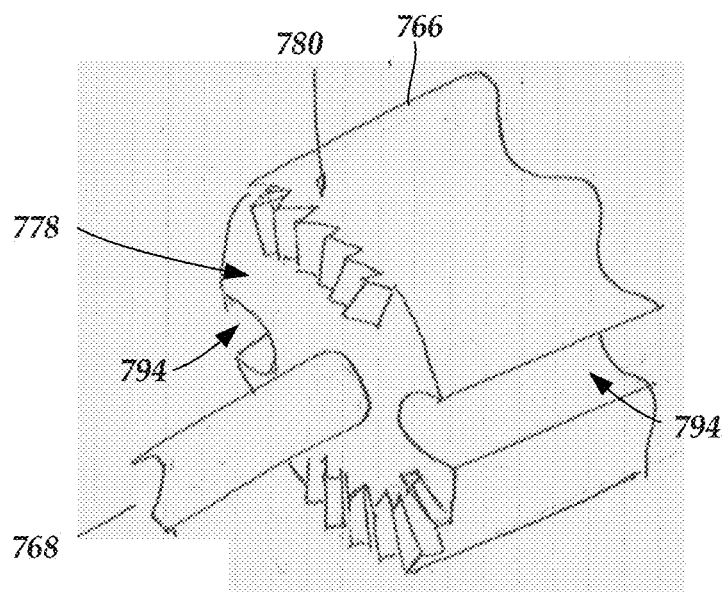
FIG. 7 is a schematic perspective view of a spindle of a lead anchor with a ratcheting surface, according to the invention.

FIG. 7 illustrates another locking arrangement including ratcheting surfaces formed on the spindle 766 and one or both of the first and second anchor housings 462 and 464. FIG. 7 is a schematic perspective view of a spindle 766 of a lead anchor with a ratcheting surface 778. Although not shown here, either or both of the opposing surfaces of the first and second anchor housings 462 and 464 (shown in FIG. 4A) contain opposing ratcheting surfaces (not shown). The ratcheting surface 778 and the ratcheting surface on the corresponding first or the second anchor housings 462 and 464 include a number of beveled teeth 780. In at least some embodiments, the beveled teeth 780 are sloped in one direction (clockwise or anti-clockwise) and are perpendicular in the other direction (clockwise or anti-clockwise). For example, in some embodiments, the beveled teeth 780 are sloped in a clockwise direction and are perpendicular in anti-clockwise direction. The spindle 766 can be rotated in the clockwise direction such that the opposing ratcheting surfaces mate together and move over the sloping surface of the teeth 780. Rotation in the anti-clockwise direction is stopped by the perpendicular surface of the teeth 780. Additionally, an operator needs to apply sufficient force to overcome friction to rotate the spindle 766 in clockwise direction. After rotation of the spindle 766 by the operator in clockwise direction, the frictional force prevents or reduces free rotation of the spindle 766 in the clockwise direction and locks the spindle 766 in the rotated position.

In at least some embodiments, the armature 768 is longitudinally flexible or elastic. The flexible armature 778 provides an inward longitudinal tensile force within the lead anchor 760. The tensile force increases friction between the ratcheting surfaces of the spindle 766 and the corresponding ratcheting surfaces of the first or second anchor housings 462 and 464. The flexible armature 778 allows the locking mechanism to be released from a locked state, described above, by grasping and pulling the first and second anchor housing 462,464 away from each other to decouple the ratcheting surfaces and allow rotation of the spindle 766 back to its original position. The armature 778 can be made of a flexible or elastic polymeric material such as silicone, rubber, or the like.

Referring to FIGS. 4A-7, any suitable manufacturing method capable of making the lead anchor 460 with the locking features, such as locking arms 672, annular recess 674, or ratcheting surface 778 with teeth 780 illustrated in FIGS. 6A, 6B, and 7 can be used to manufacture the lead anchor 460. Some examples of manufacturing the first and second anchor housings 462 and 464, spindle 466, and armature 468 may include, but are not limited to, molding, extrusion, selective laser sintering (SLS), selective heat sintering (SHS), or fused deposition modeling (FDM). Additionally, medical adhesive or a polymer reflow process can be utilized for attaching the armature 468 to the first and second anchor housings 462 and 464.

One embodiment of an electrical stimulation system is a kit including the implantable lead anchor 460 and one or more leads 103 (paddle lead shown in FIG. 1 or the percutaneous lead shown in FIG. 2). Optionally, the kit includes a lead extension 324 or a control module or both. In some embodiments, the lead 103 couples to the control module to complete the circuit of the electrical stimulation system. In some other embodiments, the lead 103 couples to the lead extension 324, and the lead extension 324 couples to the control module to complete the circuit of the electrical stimulation system. The implantable lead anchor 460 receives a portion of the lead 103 or lead extension 324 in the lead channels 490, 492, and 494 and anchors the lead 103 or lead extension 324 to patient tissue.

Referring to FIGS. 4A and 4B, according to some embodiments, a method of implanting an electrical stimulation system includes the following steps. An operator side loads portions of one or more electrical stimulation leads (for example, leads 403a and 403b) into the lead receiving channels 490, 492, and 494 of the implantable lead anchor 460. The operator then rotates the spindle 466 to lock the electrical stimulation leads in the implantable lead anchor 460. A locking arrangement locks the stimulation leads within the lead anchor 460. One example of a suitable locking arrangement is illustrated with FIGS. 6A and 6 where, upon rotation of the spindle 666, the radial openings 676 in the annular recess 674 receive the locking arms 672 locking the spindle 666. Another example of a suitable locking arrangement is illustrated with FIG. 7 where, after rotation of the spindle 766 by the operator, the beveled teeth 780 on opposing ratcheting surfaces disallows rotation of the spindle 766 in one direction and the frictional force prevents or restricts rotation of the spindle 766 in the other direction. Once, the operator has rotated the spindle 766, the spindle 766 is locked in the rotated position. The operator also sutures the lead anchor 460 to patient tissue.

Figure 8:
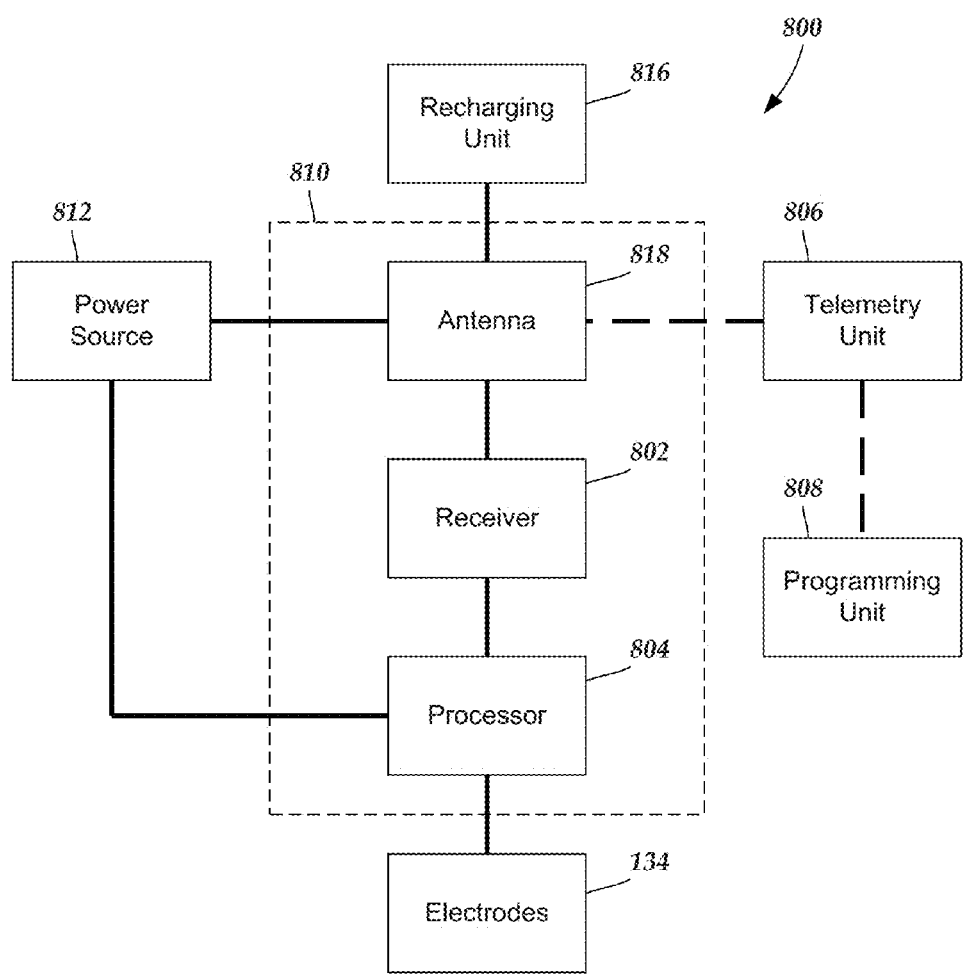
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 that, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 that is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples, and data provide a description of the manufacture and use of the composition of the invention. Since many embodiments of the invention can be made without departing from the spirit and scope of the invention, the invention also resides in the claims hereinafter appended.

The invention claimed is:

1. An implantable lead anchor, comprising:
   a first anchor housing comprising at least one first lead receiving channel;
   a second anchor housing comprising at least one second lead receiving channel;
   an armature coupled to the first anchor housing and the second anchor housing and holding the first and second anchor housings in a spaced-apart arrangement;
   a spindle configured and arranged to be rotatably disposed on the armature and between the first and second anchor housings, wherein the spindle comprises at least one third lead receiving channel configured and arranged to receive and hold a portion of a lead within the at least one third lead receiving channel; and
   a locking arrangement formed on the spindle and at least one of the first anchor housing or second anchor housing, wherein the locking arrangement is configured and arranged to maintain the spindle in a rotated position relative to the first and second anchor housing when the locking arrangement is activated.

2. The implantable lead anchor of claim 1, wherein the first anchor housing comprises two first lead receiving channels, the second anchor housing comprises two second lead receiving channels, and the spindle comprises two third lead receiving channels.

3. The implantable lead anchor of claim 1, wherein the locking arrangement comprises at least one locking arm extending from the first or second anchor housing, a corresponding annular recess in the spindle for receiving the at least one locking arm, and at least one radial opening extending from the annular recess and configured and arranged to receive a portion of the at least one locking arm to lock the at least one locking arm.

4. The implantable lead anchor of claim 1, wherein the locking arrangement comprises at least one locking arm extending from the spindle, a corresponding annular recess in the first or second anchor housing for receiving the at least one locking arm, and at least one radial opening extending from the annular recess and configured and arranged to receive a portion of the at least one locking arm to lock the at least one locking arm.

5. The implantable lead anchor of claim 1, wherein the locking arrangement comprises opposing ratcheting surfaces formed on the spindle and on at least one of the first or second anchor housing.

6. The implantable lead anchor of claim 5, wherein each of the opposing ratcheting surfaces comprises a plurality of beveled teeth arranged around at least a portion of the ratcheting surface.

7. The implantable lead anchor of claim 1, wherein the first anchor housing defines at least one suture hole through the first anchor housing.

8. The implantable lead anchor of claim 7, wherein the second anchor housing defines at least one suture hole through the second anchor housing.

9. The implantable lead anchor of claim 1, wherein the armature is longitudinally flexible so that the locking arrangement can be released from a locked state by grasping the first and second anchor housing and pulling the first and second anchor housings away from each other.

10. The implantable lead anchor of claim 1, wherein the lead anchor is formed entirely of non-metallic materials.

11. A kit, comprising:
the implantable lead anchor of claim 1; and
at least one electrical stimulation lead, wherein the implantable lead anchor is configured and arranged to receive a portion of one of the at least one electrical stimulation lead in the at least one third lead receiving channel.

12. The kit of claim 11, further comprising a control module coupleable to the at least one electrical stimulation lead.

13. The kit of claim 12, further comprising a lead extension coupleable to the lead and to the control module.

14. A method of implanting an electrical stimulation lead, the method comprising:
side loading a portion of a first electrical stimulation lead into a one of the at least one third lead receiving channel of the implantable lead anchor of claim 1; and
rotating the spindle to lock the first electrical stimulation lead in the implantable lead anchor.

15. The method of claim 14, wherein the first anchor housing comprises two first lead receiving channels, the second anchor housing comprises two second lead receiving channels, and the spindle comprises two third lead receiving channels.

16. The method of claim 15, further comprising side loading a portion of a second electrical stimulation lead into another one of the third lead receiving channels of the implantable lead anchor.

17. The method claim 15, wherein the locking arrangement comprises at least one locking arm extending from the first or second anchor housing, a corresponding annular recess in the spindle for receiving the at least one locking arm, and at least one radial opening extending from the annular recess and configured and arranged to receive a portion of the at least one locking arm to lock the at least one locking arm; and
wherein rotating the spindle comprises receiving the portion of the at least one locking arm into the at least one radial opening to lock the at least one locking arm.

18. The method claim 15, wherein the locking arrangement comprises at least one locking arm extending from the spindle, a corresponding annular recess in the first or second anchor housing for receiving the at least one locking arm, and at least one radial opening extending from the annular recess and configured and arranged to receive a portion of the at least one locking arm to lock the at least one locking arm; and
wherein rotating the spindle comprises receiving the portion of the at least one locking arm into the at least one radial opening to lock the at least one locking arm.

19. The method claim 15, wherein the locking arrangement comprises opposing ratcheting surfaces formed on the spindle and on at least one of the first or second anchor housing; and
wherein rotating the spindle comprises rotating the opposing ratcheting surfaces relative to each other to a desired locked position.

20. The method of claim 15, further comprising suturing the lead anchor to patient tissue.

* * * * *